US011730503B2

(12) United States Patent
Stefan et al.

(10) Patent No.: US 11,730,503 B2
(45) Date of Patent: Aug. 22, 2023

(54) MEDICAL INSTRUMENT HAVING A PIN-AND-SLOT CONTROL FOR MOUNTING ACTUATION ELEMENTS

(71) Applicant: KARL STORZ SE & Co. KG, Tuttlingen (DE)

(72) Inventors: Jochen Stefan, Tuttlingen (DE); Daniel Kärcher, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 117 days.

(21) Appl. No.: 17/382,799

(22) Filed: Jul. 22, 2021

(65) Prior Publication Data

US 2022/0022904 A1 Jan. 27, 2022

(30) Foreign Application Priority Data

Jul. 23, 2020 (DE) ...................... 10 2020 119 462.5

(51) Int. Cl.
*A61B 17/29* (2006.01)
*A61B 17/28* (2006.01)

(52) U.S. Cl.
CPC ........ *A61B 17/2841* (2013.01); *A61B 17/282* (2013.01); *A61B 17/2816* (2013.01); *A61B 17/29* (2013.01); *A61B 2017/2902* (2013.01); *A61B 2017/2927* (2013.01); *A61B 2017/2936* (2013.01)

(58) Field of Classification Search
CPC .............. A61B 17/2816; A61B 17/282; A61B 2017/2902; A61B 2017/2927; A61B 2017/2936; A61B 17/29; A61B 2017/2926; A61B 2017/2946; A61B 2017/2932
See application file for complete search history.

(56) References Cited

U.S. PATENT DOCUMENTS 8,882,799 B2 * 11/2014 Frank ................... A61B 17/062
606/174
2008/0147113 A1 6/2008 Nobis et al.
2009/0299143 A1 * 12/2009 Conlon .................. A61B 17/29
600/153

(Continued)

FOREIGN PATENT DOCUMENTS

DE 102009011205 A1 9/2010
DE 102016103640 A1 9/2017
EP 3175802 A1 6/2017

*Primary Examiner* — Timothy J Neal
*Assistant Examiner* — Mitchell Brian Hoag
(74) *Attorney, Agent, or Firm* — McGlew and Tuttle, P.C.

(57) ABSTRACT

A medical instrument includes a hollow shaft (2) with a proximal end (3) connected to a handle (4) and a distal end (5) with a tool (6) arranged with one jaw part (8) pivotable relative to another jaw part (7). A distal end region of the shaft as a tool tip (10) deflects relative to a longitudinal axis (9) via an axially displaceable first actuation element (11) connected to the handle. The pivotable jaw part is adjustable via a second actuation element (13) mounted axially displaceably in the hollow shaft and connected to the handle. The first actuation element and the second actuation element are parallel to each other in the longitudinal axis direction of the shaft and mounted to be guided on each other. One of the two actuation elements is mounted on the inner side. The mutual axial mounting is effected via a pin-and-slot control (19).

7 Claims, 6 Drawing Sheets

(56) References Cited

U.S. PATENT DOCUMENTS

| | | | |
|---|---|---|---|
| 2010/0331857 A1 | 12/2010 | Doyle et al. | |
| 2012/0232580 A1* | 9/2012 | Aue | A61B 17/29 606/206 |
| 2012/0289999 A1* | 11/2012 | Frank | A61B 17/062 606/205 |
| 2013/0123783 A1* | 5/2013 | Marczyk | A61B 18/1445 606/1 |
| 2013/0304083 A1* | 11/2013 | Kaercher | A61B 17/29 606/130 |
| 2015/0173786 A1* | 6/2015 | Frings | A61B 17/29 606/207 |
| 2017/0150982 A1* | 6/2017 | Stefan | A61B 17/2841 |
| 2017/0252053 A1* | 9/2017 | Kaercher | A61B 17/062 |
| 2021/0038291 A1* | 2/2021 | Grüner | A61B 1/008 |

* cited by examiner

MEDICAL INSTRUMENT HAVING A PIN-AND-SLOT CONTROL FOR MOUNTING ACTUATION ELEMENTS

CROSS REFERENCE TO RELATED APPLICATIONS

This application claims the benefit of priority under 35 U.S.C. § 119 of German Application 10 2020 119 462.5, filed Jul. 23, 2020, the entire contents of which are incorporated herein by reference.

TECHNICAL FIELD

The invention relates to a medical instrument with a hollow shaft, at the proximal end of which a handle is arranged, and at the distal end of which a tool is arranged with two jaw parts, wherein at least one jaw part is pivotable relative to the other jaw part, wherein a distal end region of the shaft that carries the tool is configured as a tool tip that can be deflected with respect to the longitudinal axis of the shaft, and wherein the deflection of the tool tip is effected via a first actuation element mounted axially displaceably in the hollow shaft and operatively connected at the proximal end to the handle, and wherein the at least one pivotable jaw part of the tool is adjustable between a closed and an opened position via a second actuation element mounted axially displaceably in the hollow shaft and operatively connected at the proximal end to the handle.

TECHNICAL BACKGROUND

Medical instruments for endoscopic surgery generally have a hollow shaft, at the proximal end of which a handle is arranged, and at the distal end of which a tool is arranged that is made up of two jaw parts movable relative to each other. The tool, designed as a gripping, holding and/or cutting instrument, can be actuated via the handle. To be able to provide the greatest possible range of action within the often confined working conditions in which the tool is used, many endoscopic instruments are designed such that the tool can be deflected with respect to the longitudinal axis of the shaft and also such that the tool is rotatable about the longitudinal axis of the shaft.

A medical instrument of the type in question is known, for example, from EP 3 175 802 A1. This known medical instrument has proven useful in practice. However, on account of the actuation elements for deflecting the tool tip and for actuating the pivotable part being mounted eccentrically relative to the longitudinal axis of the instrument, it can happen that, when the jaw parts are subjected to considerable force, the two actuation elements sag and, in the bend region to the tool tip, protrude beyond the diameter of the instruments shaft, which can be problematic particularly when using a trocar.

SUMMARY

Proceeding from this, an object of the invention is to make available a medical instrument which is of the type mentioned at the outset and which, even with the tool tip deflected, ensures an at all times constant external diameter of the instrument shaft.

This object is achieved, according to the invention, by the fact that the axially displaceable first actuation element for deflecting the tool tip and the axially displaceable second actuation element for actuating the at least one pivotable jaw part of the tool are arranged parallel to each other in the direction of the longitudinal axis of the shaft and are mounted to be guided on each other in the axial direction of the longitudinal axis of the shaft, and at least one of the two actuation elements is additionally mounted to be guided on the inner side of the distal end of the shaft, wherein the mutual axial mounting of the actuation elements on each other and also on the inner side of the distal end of the shaft is effected via a pin-and-slot control.

By virtue of the mutual guiding of the axially displaceable actuation elements on each other, according to the invention, with simultaneous guiding of at least one of the actuation elements also on the inner side of the shaft, it is ensured, through the design of the mutual axial mounting as pin-and-slot controls, that the actuation elements, even when subjected to considerable force in the bend region of the tool tip, cannot protrude beyond the external diameter of the instrument shaft, since the design according to the invention results in a mutual inhibition against divergence in a radial direction.

The design of the mutual guides as pin-and-slot controls constitutes guiding that is easy and safe to handle, with at the same time axial mobility of the components coupled to each other.

For the design of the pin-and-slot control, it is proposed, in a practical embodiment of the invention, that the pin-and-slot control is configured as a guide groove formed on at least one of the components mounted on each other, the actuation elements or the inner side of the distal end of the shaft, and as a guide web formed on the respectively corresponding other component, wherein the guide web is received with guiding in the corresponding guide groove.

It is further proposed by the invention that, in addition to the axially displaceable first actuation element for deflecting the tool tip and the axially displaceable second actuation element for actuating the at least one pivotable jaw part of the tool, an axially displaceable fourth actuation element for releasing a jaw part latch is arranged in the shaft. By means of the jaw part latch, it is possible to fix the jaw parts in a defined position relative to each other in order to facilitate the work of the operator.

To ensure that the additional fourth actuation element for releasing the jaw part latch also cannot protrude beyond the external diameter of the instrument shaft, it is proposed according to the invention that the additional axially displaceable fourth actuation element for releasing the jaw part latch is likewise mounted to be guided on the components mounted with guiding on each other, the actuation elements or the inner side of the distal end of the shaft.

According to a practical embodiment for mounting the different actuation elements inside the instrument shaft, it is proposed by the invention that the first actuation element for deflecting the tool tip is arranged centrally between the second actuation element for actuating the at least one pivotable jaw part and the fourth actuation element for releasing the jaw part latch.

For the practical design of the mutual guiding of the actuation elements coupled to each other, it is proposed according to the invention that, in order to form the pin-and-slot control, two guide webs are arranged offset by 180° relative to each other on the first actuation element for deflecting the tool tip, which guide webs engage in corresponding guide grooves which are formed on the second actuation element for actuating the at least one pivotable jaw part and on the fourth actuation element for releasing the jaw part latch, and that a respective guide web is arranged on those sides, facing toward the inner side of the distal end of the shaft, of the second actuation element for actuating the at least one pivotable jaw part and of the fourth actuation element for releasing the jaw part latch, said respective guide web engaging in a corresponding guide groove which is formed on the inner side of the distal end of the shaft.

It is further proposed by the invention that a shaft arranged proximally behind the pin-and-slot control and belonging to the first actuation element for deflecting the tool tip is configured with a circular cross section, and the parallel shafts of the second actuation element for actuating the at least one pivotable jaw part and of the fourth actuation element for releasing the jaw part latch are each configured with a semicircular cross section, such that, in the assembled state, the shafts of semicircular cross section coaxially surround the shaft of the first actuation element for deflecting the tool tip. The partial coaxial mounting of the actuation elements with respect to each other permits additional mutual guiding and stabilization and also constitutes a particularly space-saving arrangement of the actuation elements inside the instrument shaft.

To ensure the axial displaceability of the actuation elements with at the same time mutual guiding, it is proposed by the invention that the guide grooves, in the axial direction, are longer than the respective guide webs by the displacement path of the corresponding guide webs engaging in the respective guide grooves.

Finally, it is proposed by the invention that the displacement path of the respective guide webs inside the corresponding guide grooves can be limited via the axial length of the respective guide grooves.

Further features and advantages of the invention will become clear from the attached drawings in which an illustrative embodiment of a medical instrument according to the invention is shown simply by way of example, without limiting the invention to this illustrative embodiment. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF PREFERRED EMBODIMENTS

Figure 1:
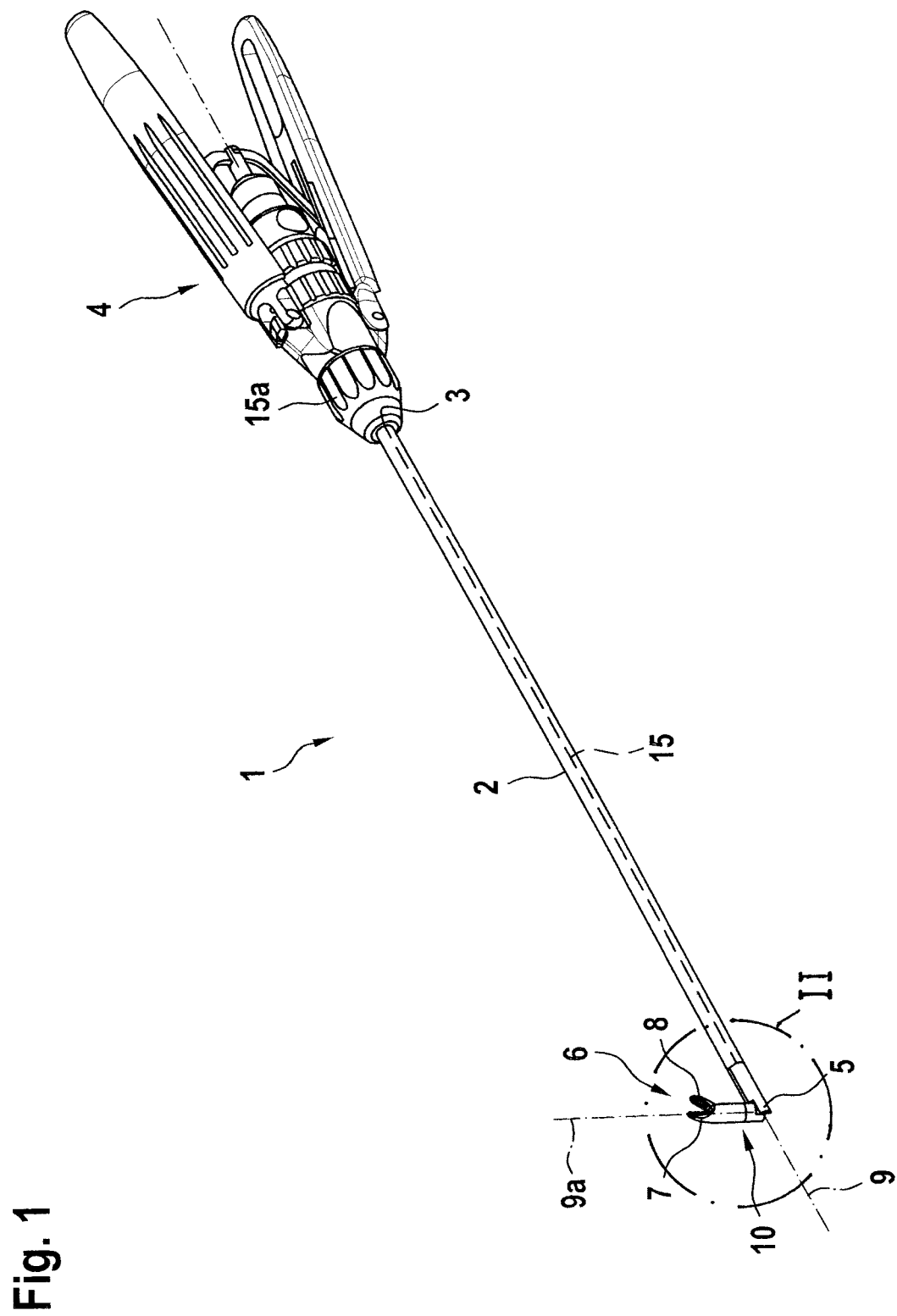
FIG. 1 is a perspective side view of a medical instrument according to the invention.

Referring to the drawings, FIG. 1 shows a medical instrument 1 with a hollow shaft 2, at the proximal end 3 of which a handle 4 is arranged, and at the distal end 5 of which a tool 6 is arranged which, in the illustrative embodiment shown, is composed of a stationary jaw part 7 and of a jaw part 8 pivotable with respect to the stationary jaw part 7.

According to an alternative embodiment, it is of course also possible for both jaw parts 7 and 8 to be configured to be pivotable relative to each other.

To give the tool 6 the greatest number of possible degrees of freedom of movement relative to the shaft 2, a distal end region of the shaft 2 that carries the tool 6 is configured as a tool tip 10 that can be deflected with respect to the longitudinal axis 9 of the shaft 2. In the view according to FIG. 1, the tool tip 10 is deflected by approximately 90° with respect to the longitudinal axis 9 of the shaft 2.

Figure 2:
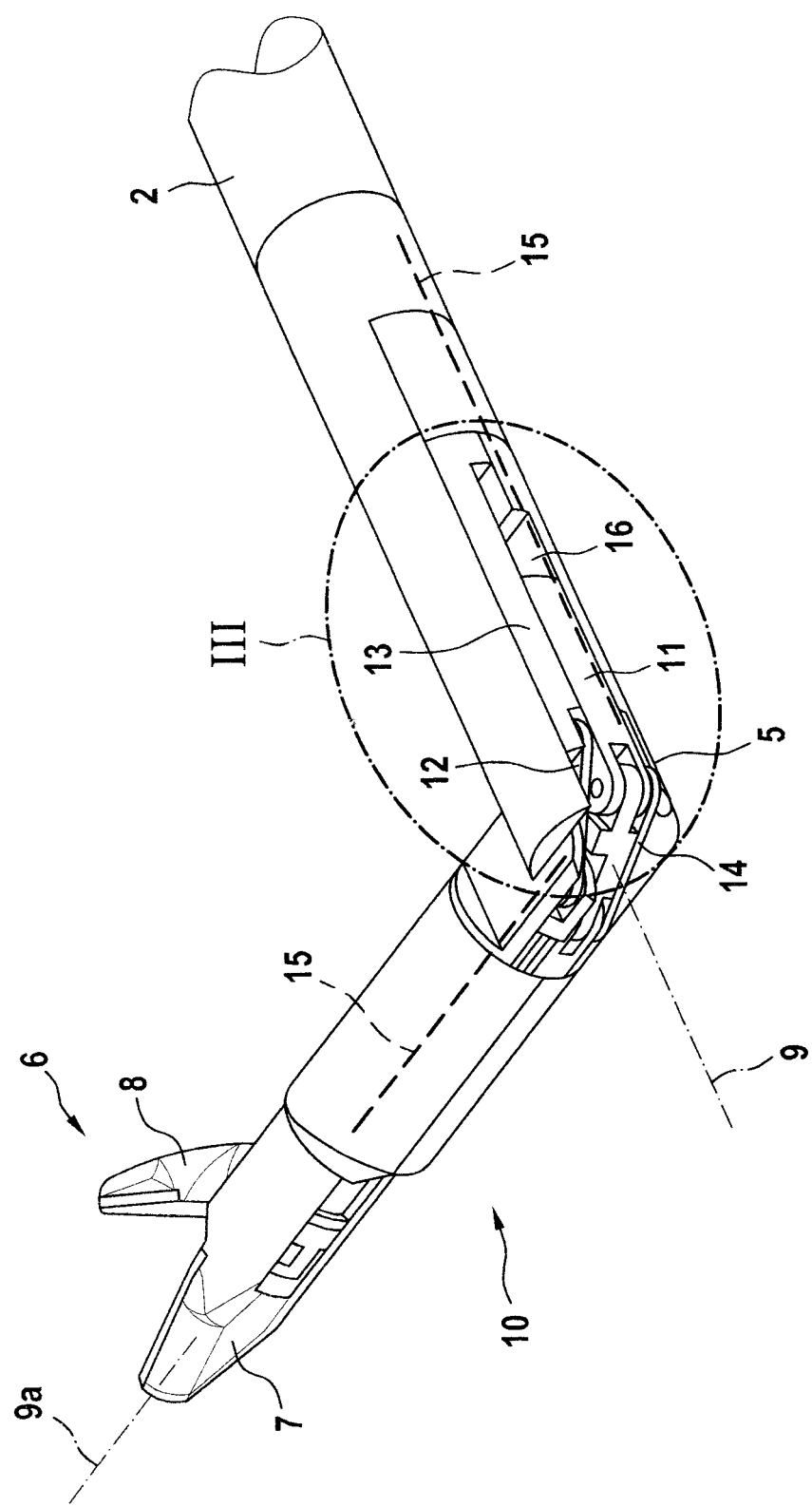
FIG. 2 is an enlarged view of the detail II according to FIG. 1, rotated 90° about the longitudinal axis of the medical instrument in relation to FIG. 1.
Figure 3:
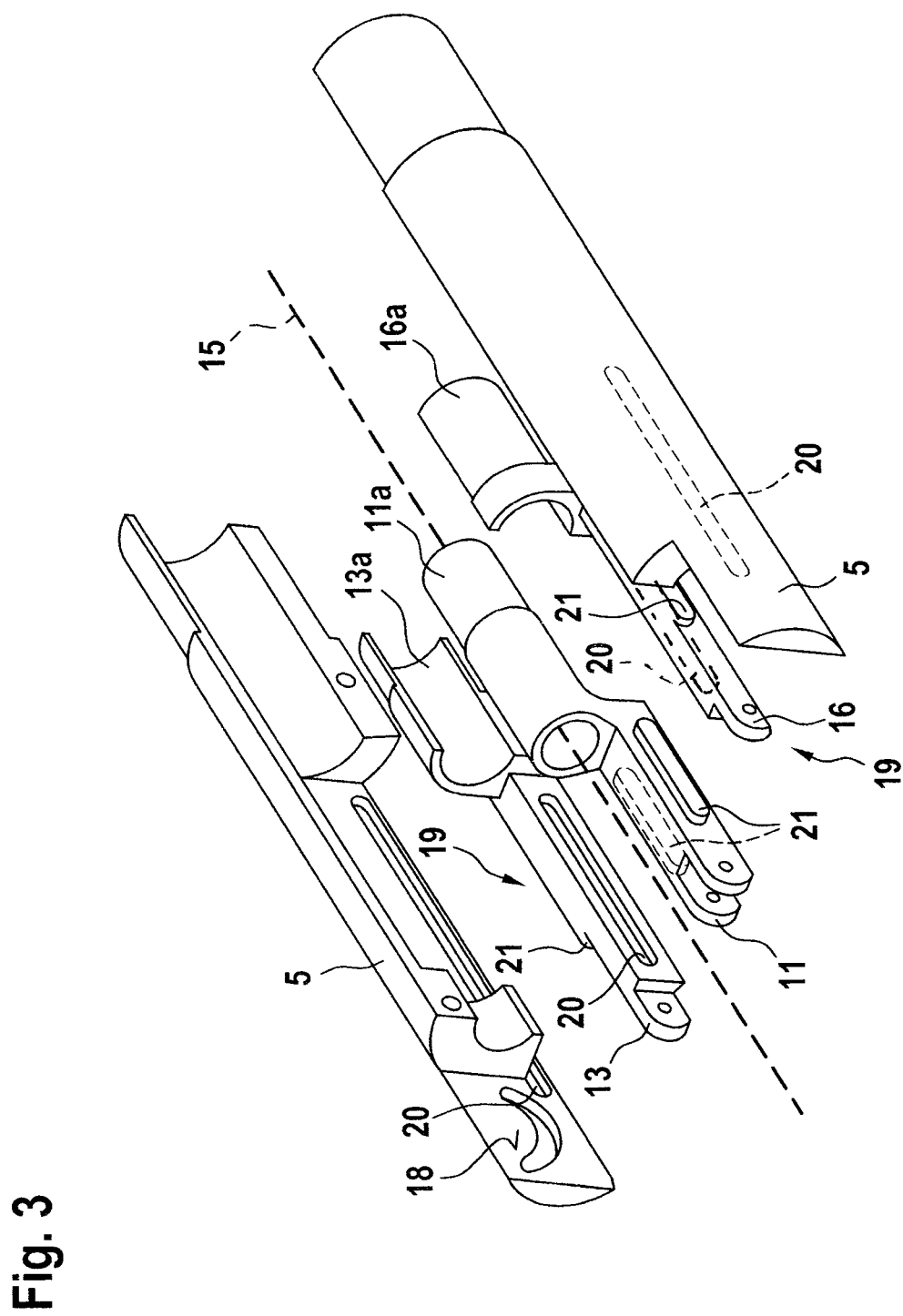
FIG. 3 is an exploded view of the detail III according to FIG. 2.
Figure 4:
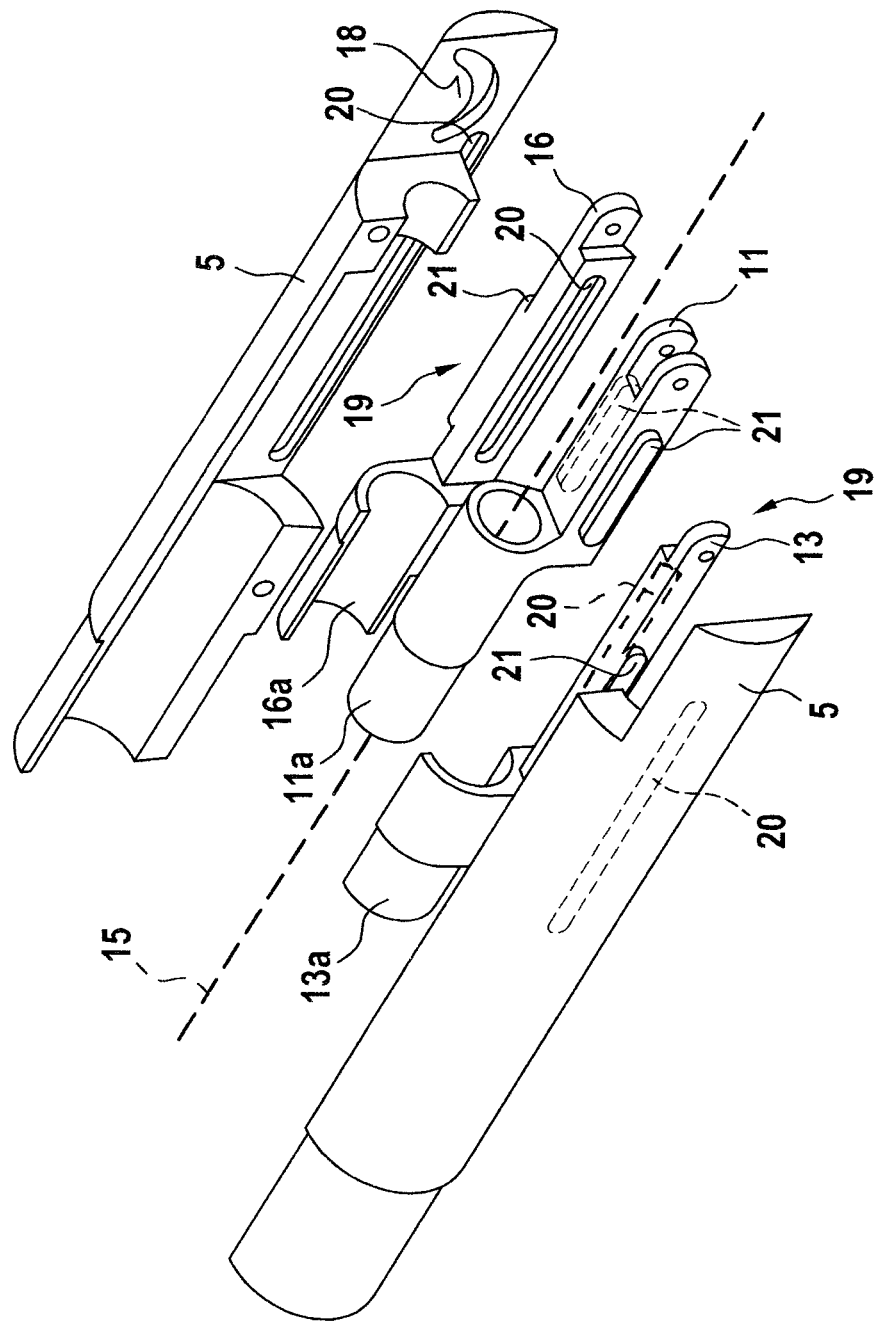
FIG. 4 is a view according to FIG. 3, but rotated through 90°.

As can be seen from FIGS. 2 to 4, the deflection of the tool tip 10 is effected via a first actuation element 11 which is mounted axially displaceably in the hollow shaft 2 and operatively connected at the proximal end to the handle 4 and which is configured as a pull/push rod. The first actuation element 11 is connected to the tool tip 10 via a coupling lever 12, which at the proximal end is mounted in an articulated manner on the first actuation element 11 and at the distal end is mounted in an articulated manner on the tool tip 10.

As can be seen from FIGS. 2 to 4, the adjustment of the pivotable jaw part 8 of the tool 6 between a closed and an opened position is effected via a second actuation element 13 which is mounted axially displaceably in the hollow shaft 2 and operatively connected at the proximal end to the handle 4 and which is likewise configured as a pull/push rod. The second actuation element 13 is connected to the pivotable jaw part 8 via a coupling lever 14, which at the proximal end is mounted in an articulated manner on the second actuation element 13 and at the distal end is operatively connected to the pivotable jaw part 8.

Moreover, the tool 6 is rotatable about the longitudinal axis 9 of the shaft 2 or, with the tool tip 10 deflected, about the longitudinal axis 9a of the tool tip 10, wherein the rotation of the tool 6 about the longitudinal axis 9 of the shaft 2 is effected via a third actuation element 15 which is mounted rotatably in the hollow shaft 2 and which at the proximal end is operatively connected to the handle 4, wherein the third actuation element 15 is configured in two parts, namely a distal subregion mounted in the deflectable tool tip 10 and a proximal subregion mounted in the proximal part of the shaft 2.

Both a solid rod and a hollow tube can be used to form the third actuation element 15.

The two mutually facing end faces of the proximal and distal subregions of the third actuation element 15 are in engagement with each other at the transition to the deflectable tool tip 10, for example, via end-face toothing arrangements not shown. The end-face toothing arrangements transmit the rotation of the proximal subregion of the third actuation element 15 about the longitudinal axis 9 of the shaft 2 to the distal subregion of the third actuation element 15 for the rotation about the longitudinal axis 9a of the tool tip 10.

In addition to this rotation of the tool 6 about the longitudinal axis 9 of the shaft 2 or, with the tool tip 10 deflected, about the longitudinal axis 9a of the tool tip 10 by means of the third actuation element 15, the shaft 2 is rotatable about the longitudinal axis 9 of the shaft 2 via a rotary drive 15a arranged on the handle 4.

In addition to the first actuation element 11 mounted axially displaceably in the shaft 2 for deflecting the tool tip 10 and to the second actuation element 13 for actuating the pivotable jaw part 8 of the tool 6, the medical instrument 1 shown has a fourth actuation element 16 which, mounted axially displaceably in the shaft 2, serves for releasing a jaw part latch 17 formed on the tool 6. By means of the jaw part latch 17 shown schematically in FIG. 7, it is possible to fix the jaw parts 7 and 8 in a defined position relative to each other, in particular in the closed position of the jaw parts 7 and 8, in order to facilitate the work of the operator. The fourth actuation element 16 is likewise configured as a pull/push rod.

In order to mount the different actuation elements inside the instrument shaft 2 in a way that saves space, the first actuation element 11 for deflecting the tool tip 10 is arranged centrally between the second actuation element 13 for actuating the pivotable jaw part 8 and the fourth actuation element 16 for releasing the jaw part latch 17.

To avoid a situation in which, when the jaw parts 7 and 8 are subjected to considerable force, the actuation elements 11, 13 and 16 sag and, in the bend region from the shaft 2 to the tool tip 10, protrude beyond the diameter of the instrument shaft 2, which can be problematic in particular when using a trocar, at least some of the actuation elements 11, 13 and 16 are arranged parallel to each other in the direction of the longitudinal axis 9 of the shaft 2 and, in the axial direction of the longitudinal axis 9 of the shaft 2, are mounted to be guided on each other and at least partly in addition with guiding on the inner side 18 of the distal end 5 of the shaft 2, as can be seen from FIGS. 3 to 6.

This design with the actuation elements 11, 13 and 16 mounted to be guided on each other and on the inner side 18 of the shaft 2 results in a mutual inhibition that prevents sagging in a radial direction.

As can be seen from FIGS. 3 to 6, the mutual axial mounting of the actuation elements 11, 13 and 16 and of the inner side 18 of the distal end 5 of the shaft 2 is in each case effected via a pin-and-slot control 19, which is formed at the distal end regions of the actuation elements 11, 13 and 16 and the inner side 18 of the distal end 5 of the shaft 2. The design of the mutual guides as pin-and-slot controls 19 constitutes guiding that is easy and safe to handle, at the same time with axial mobility of the components 11, 13, 16 and 18 coupled to each other.

Proximally behind the pin-and-slot controls 19, the actuation elements 11, 13 and 16, as can be seen from FIGS. 3 and 4, are mounted parallel to each other in the interior of the shaft 2 so as to permit a particularly space-saving and compact construction, in order to keep the external diameter of the shaft 2 as small as possible.

According to the embodiment shown, the proximal shaft 11a of the first actuation element 11 for deflecting the tool tip 10 is circular in cross section, while the parallel shafts 13a and 16a of the second actuation element 13 for actuating the pivotable jaw part 8 and of the fourth actuation element 16 for releasing the jaw part latch 17 are each configured with a semicircular cross section, such that, in the assembled state, the shafts 13a and 16a of semicircular cross section coaxially surround the shaft 11a of the first actuation element 11 for deflecting the tool tip 10. The circular shaft 11a of the first actuation element 11 is additionally configured as a hollow tube. The free lumen of the hollow tube forming the shaft 11a of the first actuation element 11 serves to receive and guide the third actuation element 15 for rotating the tool 6 about the longitudinal axis 9 of the shaft 2, as is indicated by broken lines in FIGS. 3 and 4.

By virtue of this guiding of the third actuation element 15 inside the shaft 11a of the first actuation element 11 and by virtue of the two-part design of the third actuation element 15 with a proximal subregion and a distal subregion, the third actuation element 15 does not require a pin-and-slot control 19 or the like in order to prevent sagging in the bend region from the shaft 2 to the tool tip 10.

The pin-and-slot controls 19 are configured as a guide groove 20 formed on at least one of the components mounted on each other, the actuation elements 11, 13, 16 or the inner side 18 of the distal end 5 of the shaft 2, and as a guide web 21 formed on the respectively corresponding other component, wherein each guide web 21 is received with guiding in a corresponding guide groove 20.

The structural design of the pin-and-slot controls 19 can be seen from FIGS. 3 to 6.

In order to form the pin-and-slot control 19, two guide webs 21 are arranged offset by 180° relative to each other on the centrally arranged first actuation element 11 for deflecting the tool tip 10, which guide webs 21 engage in corresponding guide grooves 20 which are formed on the one hand on the second actuation element 13 for actuating the pivotable jaw part 8 and on the other hand on the fourth actuation element 16 for releasing the jaw part latch 17. Moreover, a respective guide web 21 is arranged on those sides, facing toward the inner side 18 of the distal end 5 of the shaft 2, of the second actuation element 13 for actuating the pivotable jaw part 18 and of the fourth actuation element 16 for releasing the jaw part latch 17, said respective guide web 21 engaging in a corresponding guide groove 20 which is formed on the inner side 18 of the distal end 5 of the shaft 2.

Figure 5:
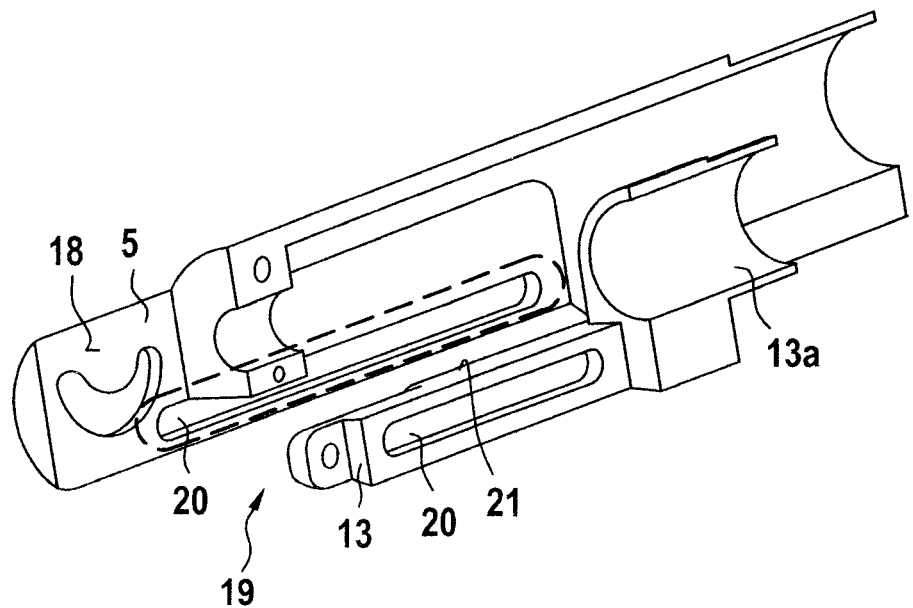
FIG. 5 is a first enlarged detailed view from FIGS. 3 and 4.
Figure 6:
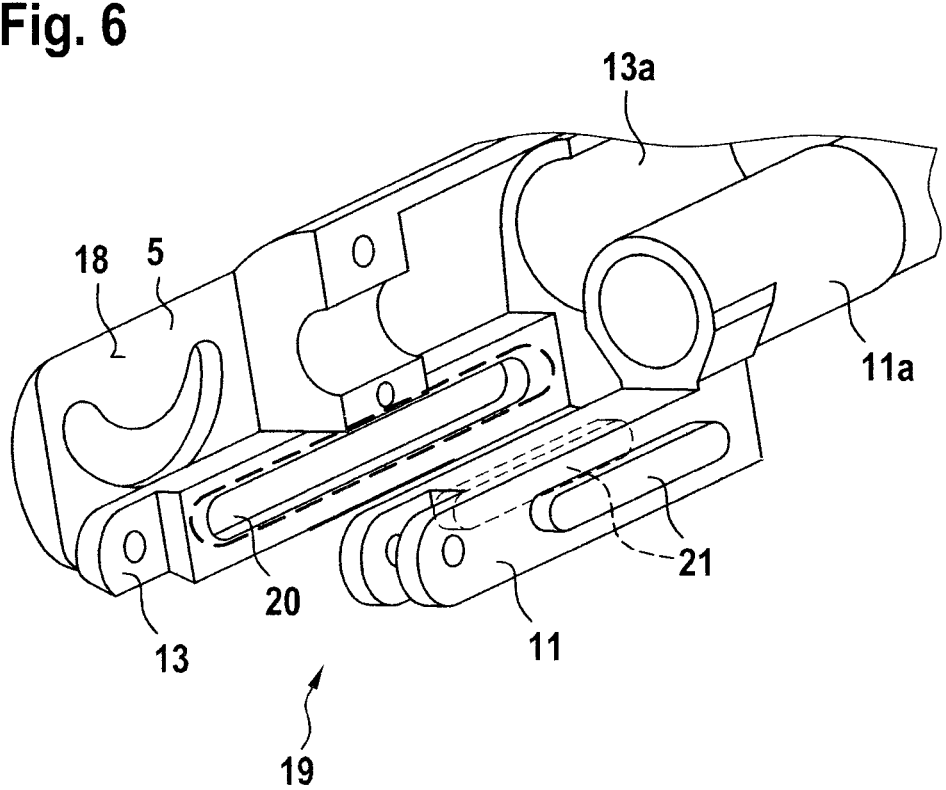
FIG. 6 is a second enlarged detailed view from FIGS. 3 and 4.

As can also be seen in particular from FIGS. 5 and 6, the guide grooves 20, in the axial direction, are longer than the respective guide webs 21 received in the guide grooves 20. This longer axial extent of the guide grooves 20 is necessary for ensuring the axial displaceability of the actuation elements 11, 13 and 16 with at the same time mutual guiding. For this reason, the guide grooves 20, in the axial direction, are longer than the respective guide webs 21 by the displacement path of the corresponding guide webs 21 engaging in the respective guide grooves 20.

Similarly, the displacement path of the respective guide webs 21 inside the corresponding guide grooves 20 can be limited via the axial length of the respective guide grooves 20.

Figure 7:
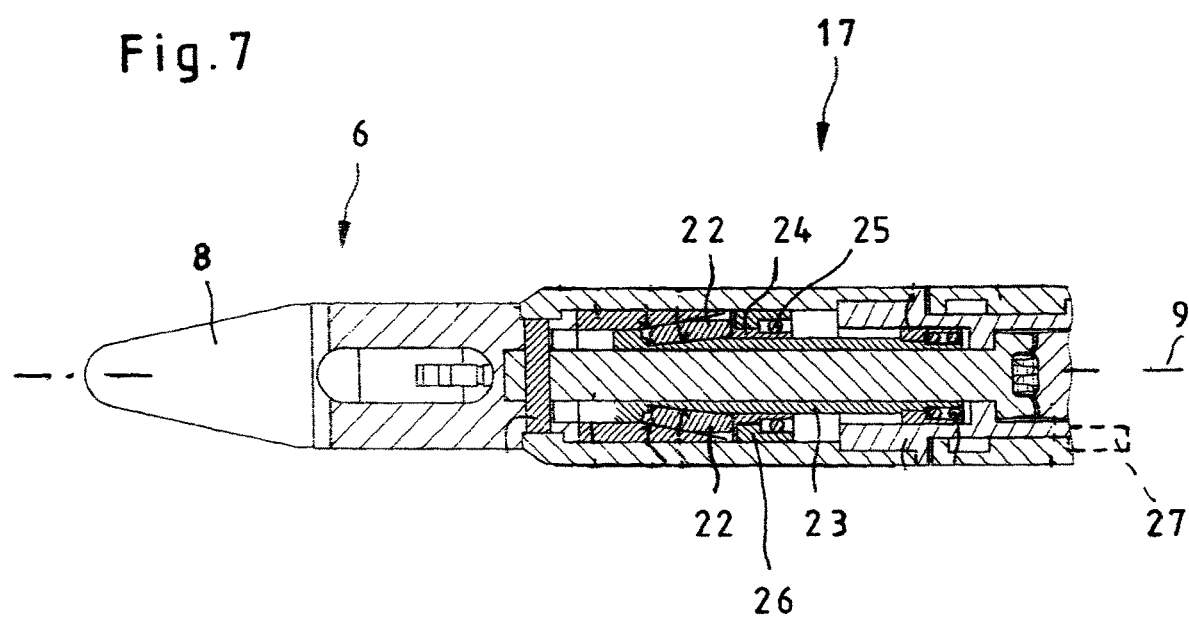
FIG. 7 is a schematic view of a jaw part latch.

FIG. 7 shows, schematically, the design of the jaw part latch 17 as known from DE 10 2016 103 640 A1, reference being made to the entire content of said document.

The jaw parts 7 and 8 can be fixed in the closed position via the jaw part latch 17, for example such that a surgical needle held between the jaw parts 7 and 8 can be securely held and guided without any further action on the part of the operator.

The jaw part latch 17 shown is composed principally of two locking elements 22 which are arranged symmetrically with respect to the longitudinal axis 9 and mounted in a longitudinally displaceable manner in the tool tip 10 and via which the axial movement of a tensioning sleeve 23 can be blocked, which tensioning sleeve 23, in order to actuate the at least one pivotable jaw part 8, is coupled at the distal end to the at least one pivotable jaw part 8.

The locking elements 22 are connected to an annular locking carriage 24 mounted in a longitudinally displaceable manner on the tensioning sleeve 23. The locking carriage 24 for its part is connected rotatably via a rotary bearing 25 to an intermediate piece 26, which is connected via a connecting lever 27 to the fourth actuation element 16 in the shaft 2.

A medical instrument 1 configured as described above is characterized in that, by virtue of the mutual guiding of the actuation elements 11, 13 and 16 on each other and on the inner side 18 of the distal end 5 of the shaft 2 by means of the mutual axial mounting, configured as pin-and-slot control 19, of the actuation elements 11 and 13 and of the inner side 18 of the distal end 5 of the shaft 2, sagging of the actuation elements 11, 13 and 16 is excluded, and therefore, even with the tool tip 10 deflected, an at all times constant external diameter of the instrument shaft 2 is ensured.

While specific embodiments of the invention have been shown and described in detail to illustrate the application of the principles of the invention, it will be understood that the invention may be embodied otherwise without departing from such principles.

LIST OF REFERENCE CHARACHTERS

1 medical instrument
2 shaft
3 proximal end (shaft)
4 handle
5 distal end (shaft)
6 tool
7 stationary jaw part
8 pivotable jaw part
9 longitudinal axis (shaft)
9a longitudinal axis (tool tip)
10 tool tip
11 first actuation element (deflecting)
11a shaft
12 coupling lever
13 second actuation element (jaw part)
13a shaft
14 coupling lever
15 third actuation element (rotating)
15a rotary drive
16 fourth actuation element (jaw part latch)
16a shaft
17 jaw part latch
18 inner side (shaft)
19 pin-and-slot control
20 guide groove
21 guide web
22 locking element
23 tensioning sleeve
24 locking carriage
25 rotary bearing
26 intermediate piece
27 connecting lever

The invention claimed is:

1. A medical instrument comprising:
a hollow shaft;
a handle arranged at a proximal end of the shaft;
a tool arranged at a distal end of the shaft, the tool comprising two jaw parts, wherein at least one jaw part is pivotable relative to the other jaw part, wherein a distal end region of the shaft that carries the tool is configured as a tool tip that is deflectable with respect to a longitudinal axis of the shaft;
a first actuation element for effecting a deflection of the tool tip, the first actuation element being mounted axially displaceably in the hollow shaft and operatively connected at the proximal end to the handle;
a second actuation element for adjustment of the at least one pivotable jaw part of the tool between a closed position and an opened position, the second actuation element being mounted axially displaceably in the hollow shaft and operatively connected at the proximal end to the handle, wherein the axially displaceable first actuation element for deflecting the tool tip and the axially displaceable second actuation element for actuating the at least one pivotable jaw part of the tool are arranged parallel to each other in the direction of the longitudinal axis of the shaft and are mounted to be guided on each other in the axial direction of the longitudinal axis of the shaft, and at least one of the two actuation elements is additionally mounted to be guided on an inner side of the distal end of the shaft; and
a pin-and-slot control, wherein a mutual axial mounting of the actuation elements on each other and also on the inner side of the distal end of the shaft is effected via the pin-and-slot control, wherein, in addition to the axially displaceable first actuation element for deflecting the tool tip and the axially displaceable second actuation element for actuating the at least one pivotable jaw part of the tool, an additional axially displaceable fourth actuation element for releasing a jaw part latch is arranged in the shaft, wherein the first actuation element for deflecting the tool tip is arranged centrally between the second actuation element for actuating the at least one pivotable jaw part and the fourth actuation element for releasing the jaw part latch.

2. The medical instrument as claimed in claim 1, wherein the pin-and-slot control is configured as a guide groove formed on at least one of the first actuation element, the second actuation element and the inner side of the distal end of the shaft, and as a guide web formed on another of the first actuation element, the second actuation element and the inner side of the distal end of the shaft, wherein the guide web is guidingly received in the guide groove.

3. The medical instrument as claimed in claim 2, wherein the guide grooves, in the axial direction, are longer than the respective guide webs by a displacement path of the corresponding guide webs engaging in the respective guide grooves.

4. The medical instrument as claimed in claim 2, wherein the displacement path of the respective guide webs inside the corresponding guide grooves is limited via an axial length of the respective guide grooves.

5. The medical instrument as claimed in claim 1, wherein the additional axially displaceable fourth actuation element for releasing the jaw part latch is likewise mounted to be guided on one or more of the first actuation element, the second actuation element and the inner side of the distal end of the shaft.

6. The medical instrument as claimed in claim 1, wherein, in order to form the pin-and-slot control, two guide webs are arranged offset by 180° relative to each other on the first actuation element for deflecting the tool tip, which guide webs engage in corresponding guide grooves which are formed on the second actuation element for actuating the at least one pivotable jaw part and on the fourth actuation element for releasing the jaw part latch, and a respective guide web is arranged on sides, facing toward the inner side of the distal end of the shaft, of the second actuation element for actuating the pivotable jaw part and of the fourth actuation element for releasing the jaw part latch, said respective guide web engaging in a corresponding guide groove which is formed on the inner side of the distal end of the shaft.

7. The medical instrument as claimed in claim 1, wherein a shaft arranged proximally behind the pin-and-slot control and belonging to the first actuation element for deflecting the tool tip is configured with a circular cross section, and parallel shafts of the second actuation element for actuating the at least one pivotable jaw part and of the fourth actuation element for releasing the jaw part latch are each configured with a semicircular cross section, such that, in an assembled state, the shafts of semicircular cross section coaxially surround the shaft of the first actuation element for deflecting the tool tip.

* * * * *